United States Patent [19]

Pawelec

[11] Patent Number: 4,481,952

[45] Date of Patent: Nov. 13, 1984

[54] DEVICE FOR THE STUDY OF THE ALIMENTARY CANAL

[76] Inventor: Jerzy Pawelec, 18, 1 Longangstraede, 1468 Copenhagen K, Denmark

[21] Appl. No.: 245,346

[22] PCT Filed: Mar. 21, 1979

[86] PCT No.: PCT/DK79/00011

§ 371 Date: Nov. 22, 1979

§ 102(e) Date: Nov. 21, 1979

[87] PCT Pub. No.: WO79/00811

PCT Pub. Date: Oct. 18, 1979

[30] Foreign Application Priority Data

Mar. 22, 1978 [DK] Denmark .............................. 1334/78

[51] Int. Cl.³ ............................................. A61B 10/00
[52] U.S. Cl. ..................................... 128/769; 128/780
[58] Field of Search ............... 128/631, 769, 760, 222, 128/780

[56] References Cited

U.S. PATENT DOCUMENTS

| | | | |
|---|---|---|---|
| 3,057,344 | 10/1962 | Abella et al. | 128/769 |
| 3,118,439 | 1/1964 | Perrenoud | 128/769 |
| 3,315,660 | 4/1967 | Abella | 128/769 |
| 3,319,622 | 5/1967 | Shiner | 128/769 X |
| 3,485,235 | 12/1969 | Felson | 128/769 |
| 3,719,183 | 3/1978 | Schwartz | 128/631 |
| 4,036,214 | 7/1977 | Bucalo | 128/769 |
| 4,172,446 | 10/1979 | Bucalo | 128/769 |
| 4,239,040 | 12/1980 | Hosoya et al. | 128/769 X |

*Primary Examiner*—Kyle L. Howell
*Assistant Examiner*—John C. Hanley
*Attorney, Agent, or Firm*—Leonard J. Kalinowski

[57] ABSTRACT

A swallowable capsule for obtaining samples of gastric and/or intestinal fluids, the capsule defining an inner fluid receiving chamber having an inlet port which is normally sealed off from the exterior of the capsule by way of a blocking means including a mass the properties of which change upon contact with the suitable fluids present in the digestion tract, causing the means to communicate the inlet port with the outside of the capsule allowing a sample of the fluid to be aspirated into the chamber. Located within the chamber is a closing means normally maintained in a flow permitting position by a mass which glues the necessary parts of the closing means together in such a way that the parts cannot move, so that the action of the closing means is neutralized. This mass is responsive to contact with the suitable fluids of the alimentary canal to permit the closing means to operate and seal off the chamber so that the sample is secured from contamination during its further travel through the rest of the digestive tract.

44 Claims, 21 Drawing Figures

DEVICE FOR THE STUDY OF THE ALIMENTARY CANAL

BACKGROUND OF THE INVENTION

1. Field of the Invention

This invention relates to sampling devices for automatically obtaining samples of gastric and intestinal fluids in the digestive tracts of humans and animals and for use in determining the presence of free hydrochloric acid and lactic acid in the gastric fluids.

2. Description of the Prior Art

Examination of the contents of the different parts of the gastrointestinal tract plays a great role in diagnostic and medical research. Information from these examinations can be of great importance for diagnosing diseases of stomach, duodenum, gallbladder and pancreas, as well as for diagnosing certain blood diseases.

The determination of the presence or absence of free hydrochloric acid and lactic acid in the digestive tract is especially important and useful. The absence of free hydrochloric acid in the gastric fluid is a characteristic finding of pernicious anemia. The absence of hydrochloric acid together with the presence of lactic acid in the gastric fluid indicates for advanced carcinoma of the stomach.

Stomach tubes are the normal instruments for collecting samples of the contents of the stomach and duodeum. As is known, these are long, flexible tubes which are inserted to the digestive tract through the patient's mouth or nose, and then fluid from the actual part of the digestive tract is aspirated through the tube. The examination normally takes place under X-ray control, to check for proper positioning of the end of the tube in the digestive tract.

Intubation of the digestive tract using these methods is difficult, and for patient a very unpleasant intervention. It is a burden for the patient, both physically and psychologically, and it is often impossible to examine patients who are especially sensitive, physically weak or who have heart disease.

The stress to which the patient is subjected during intubation of the stomach or duodenum can have a disturbing influence on the function of the digestive organs, and consequently, in some instances the test results may be inconclusive or erroneous.

Intubation of the digestive tract is an expensive examination. It is a very time-consuming examination for the doctor, and demands the help of highly qualified nurses, a suitable place with comfortable beds where the patients can be examined, and access to X-ray apparatus. The examination immobilizes the patient for several hours, and exposes him to the risks of X-ray exposure.

The above mentioned difficulties and hazards associated with the collection of intestinal fluid preclude the use of conventional technique for mass-examinations, which are especially important to reveal cases of gastric cancer.

In recent years an application of swallowable capsules for the purpose of collecting samples of gastric fluids has been suggested. Examples of such devices are described in U.S. Pat. No. 3,118,439 issued to J. Perrenond on Jan. 21, 1964 and in U.S. Pat. No. 3,485,235 issued to R. Felson on Dec. 23, 1969. In using these patented devices, the opening of the swallowed capsule in the alimenttary canal and the intake of the sample of fluid is externally controlled by placing the patient in the high-frequency electromagnetic field. This examination however requires highly skilled medical personnel, the use of an X-ray device, to observe the passage of the capsule through the alimentary canal, and this procedure itself is likely to induce psychological stress in the patient.

SUMMARY OF THE INVENTION

The present invention provides a sampling device for automatically obtaining samples of gastric and/or intestinal fluids and for use in determining the presence of free hydrochloric acid and lactic acid in the digestive tracts of humans or animals.

The device is similar in size and shape to a conventional pharmaceutical capsule and is thus suitable for ingestion. The capsule defines an inner fluid receiving chamber having an entrance which is normally sealed off from the external environment by way of a blocking mechanism including a mass which, upon contact with a certain fluid present in the digestive tract causes the mechanism to communicate the opening with the outside of the capsule allowing a sample of the fluid to enter and be retained in the chamber. Located within the chamber is a cylindrical spring operated valve normally maintained in a flow permitting position by a mass which glues the necessary parts of the valve together in such a way that the parts cannot move, so the action of the strained spring is neutralized. This mass is also responsive to contact with the fluid to permit the valve to operate and seal off the chamber after a predetermined time. The sample is then secured from contamination during its further travel through the rest of the digestive tract, and the capsule is evacuated by a normal defectory process and recovered to be sent to a laboratory for analysis of the sample. The collected samples can be used for chemical, biochemical, microbiological, parasitological and cytological examination.

The sampling device of the present invention used in collecting a sample of gastric fluids (Capsule G-gastric) is equiped with mechanisms, which control the opening and closing of the capsule, and which are blocked by a mass, which can for example comprise gelatin, saccarose or another carbohydrate, which loses its blocking properties after a short time following contact with the gastric fluid. The opening of the capsule, the collection of the sample and reclosing of the capsule takes place in the stomach.

With the use of a different mass, which for example comprises celluloseacetatephtalate which will not dissolve until after contact with the alkaline contents of the small intestine, the capsule (Capsule D-duodenum) may be used to collect a sample of intestinal fluids.

In another embodiment, the capsule additionally contains a basic-acid indicator in the chamber, which responds to free HCl in the gastric fluid to cause a color change in the fluid sample, indicating the presence of free HCl in the sample (Capsule A-acidity). A part of the wall of the capsule is made of transparent material to permit viewing of the sample contained therein. Alternatively, an indicator sensitive to lactic acid may be disposed in the chamber to react with the fluid sample, and provide a change in color of the sample, indicating the presence of lactic acid in the sample (Capsule LA-lactic acid).

In accordance with one aspect of the invention, first and second spring machanisms control the opening of the capsule and then its closing. The spring mechanisms are initially neutralized by a mass that secures parts of the capsule together, in such a way that the mechanisms cannot operate. In this configuration, the entrance to the capsule chamber is normally kept closed off.

The mass which blocks these mechanism has such properties that after it contacts gastro or intestinal fluid, depending on the application and thus type of mass used, its characteristics are altered in such a way that it loses the properties that permit it to secure the parts of the device together and prevent operation of the capsule's mechanisms. A portion of the mass which normally neutralizes the action of the first spring mechanism is disposed externally of the capsule. Accordingly, when the capsule is swallowed by the patient and the portion of the mass contacts the gastro (or intestinal) fluid, its properties are altered allowing the first spring mechanism to operate. This expands the capsule, enlarging the capacity of its inner chamber and aspirating a sample of the fluid into the chamber. The expanding of the capsule causes exposure of a place covered by a second portion of the mass, which normally neutralizes the action of the second spring means, to the fluid being sampled. As result, the second mass loses the properties which enable it to neutralize operation of the second spring mechanism. This permits a valve to operate and close the capsule, hermetically sealing it. With the fluid sample enclosed therewithin and isolated from contamination during its way through the rest of the digestive tract.

Through the present invention it is possible to examine the gastric and duodenal fluids without any stress, discomfort and pain of intubation obviates the need for X-ray exposure and X-ray equipment, and immobilization of the patient for several hours in bed. The examination can be performed independently of the patient's state of health.

Examination using the principles of the present invention is so simple to perform, that the patient can do part of the examination (according to doctor's instructions) himsef in his own home, with no need for expensive medical care. The examination, which can be made by the help of the new invention, open new possibilites for diagnostic and research, and can lead to a better knowledge of the physiology and biochemistry of the digestive process. In particular, the fluid sampling device of the present invention can play an especially large role in mass-examinations of the digestive tract for finding cancer alterations because it is inexpensive and easy to use.

DESCRIPTION OF THE DRAWINGS

The construction of the subject invention will be understood clearly from reference to the accompanying drawings in which:

FIGS. 15 and 16 are sectional views of a sixth embodiment of the capsule illustrating unoperated and operated configuration, respectivly;

FIG. 17 is a sectional view taken along lines 17—17 of FIG. 15;

FIGS. 18 and 19 are sectional views of a seventh embodiment of the capsule illustrating unoperated and operated configurations, respectively; and, FIGS. 20 and 21 are sectional views of an eighth embodiment of the capsule illustrating unoperated and operated configurations, respectively.

DESCRIPTION OF PREFERRED EMBODIMENTS

Figure 4:
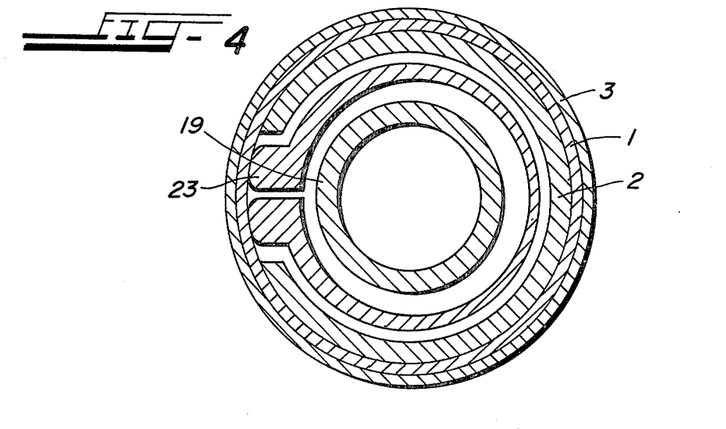
FIG. 4 is a sectional view taken along the lines 4—4 of FIG. 1.
Figures 5, 6, 8, 9:
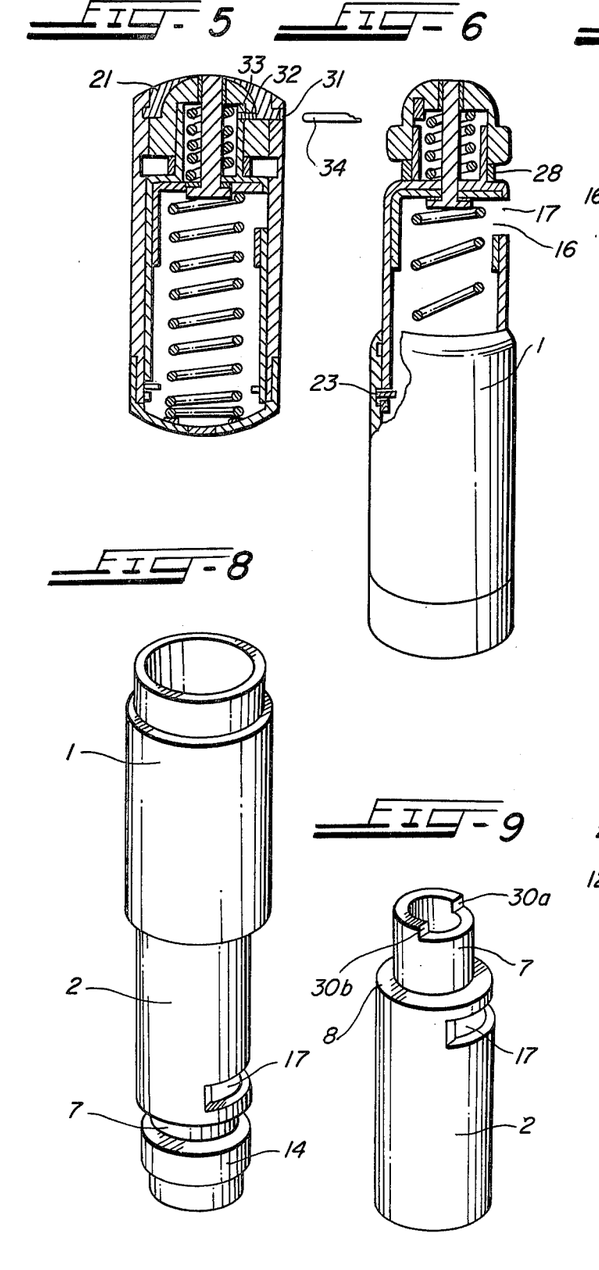
FIG. 5 is a sectional view taken along the lines 5—5 of FIG. 1.
FIGS. 6 and 7 are breakaway views showing the capsule of FIG. 1 in two different working positions.
FIG. 8 is a perspective view of the capsule with the bottom portion of the capsule removed.
FIG. 9 is a perspective view of the inner shell member of the capsule of FIG. 1.

With reference to FIGS. 1-9 of the drawings, the sampling device according to one embodiment basically comprises a capsule having an outer shell member 1 and an inner shell member 2 which is received in telescopic engagement with the outer shell member defining an enclosed chamber 18. As shown best in FIG. 1, which illustrates the device in its closed configuration, an aperture or window 17, shown best in FIG. 9, formed in the side wall of the inner shell member 2 is normally sealed off or closed by the inner wall of the outer shell member 1. In the closed configuration, shell members 1 and 2 are secured together by mass 21 neutralizing the effect of a compressed spring 19, extending axially within compartment 18, and which tends to drive the two shell members apart. As will be described, upon contact with a certain fluid normally present in the alimentary canal, the mass 21 loses its effectiveness as a holding agent. This permits the shell members to be driven apart under the force of the spring 19, so that as the walls of the two shell members slide along one another, eventually aperture 17 is communicated with the outside of the capsule, as shown in FIG. 6, allowing fluid, such as intestinal or gastric fluid, to be aspirated into chamber 18.

Figure 7:
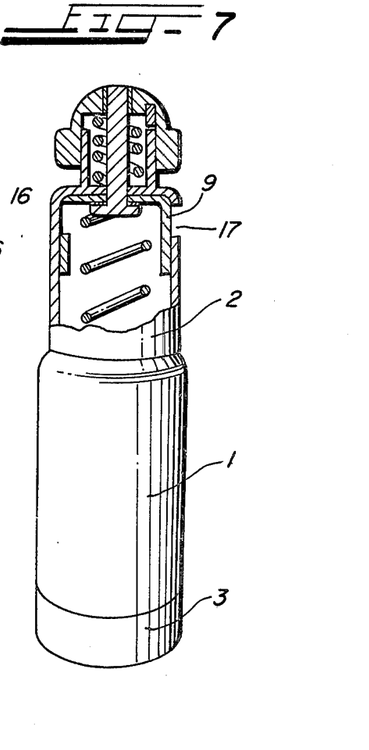

A spring operated valve assembly, including valve member 9 and valve operating spring 25, is mounted within the capsule. A further mass 28, having the same characteristics as mass 21, normally maintains the valve in flow permitting position, that is with aperture 16, (FIG. 3) formed in the side wall of the valve member 9 being in alignment with aperture 17. The valve operates a short time after the capsule expands and the fluid contacts mass 28 changing its characteristics. When operated, the valve closes the capsule by rotating aperture 16 out of alignment with aperture 17, as shown in FIG. 7, hermetically sealing the capsule with the fluid contained within the chamber thereof. The device in shape of a capsule and size of 8×19 mm, is able to collect about 1 ml of intestinal fluid. Using microanalysis, this is sufficient quantity to perform many different analysis.

The mass that is used depends upon the function or application of the capsule. If the capsule is used to collect gastric fluid, the mechanisms that guide the opening and closing of the capsule, hereinafter referred to as capsule G (Gastric) are blocked by a mass which loses its blocking properties after short contact with the gastric fluid. The opening of the capsule, the collection of the sample and the closing takes place in stomach. For blocking the mechanism, the mass may be comprised of gelatin, proteins, gum arabic, saccharose or other carbohydrates. A hot solution of these substances after stiffening creates a mass, which secures or holds together appropriate parts of the capsule in a way to effectively neutralize the action of springs. Such mass loses its properties which enable it to hold these parts together after a short contact with the gastric fluid. For example, depending on the composition of the mass, it may become brittle causing it to fracture under force of the spring it normally neutralizes, or the mass may dissolve freeing the parts it normally holds together.

The capsule may also be used to collect intestinal fluid, in which case the mass is comprised of cellulose-acetate phtalate, shellac, polyvinyl chloride or polymers of polyvinylpyridine acril acid. In use of this capsule, hereinafter referred to as capsule D (duodenum), the blocking mass or substance is not submitted to any change in the stomach. Its change occurs only after contact with the alkaline contents of the small intestine. It is pointed out that capsule D mechanisms can use that same mass as that used for the capsule, that mass being covered with a film or coating comprising celluloseacetatephtalate, shellac, polyvinyl chloride or polymers of polyvinylpyridineacril acid which resist gastric fluids.

Figure 1:
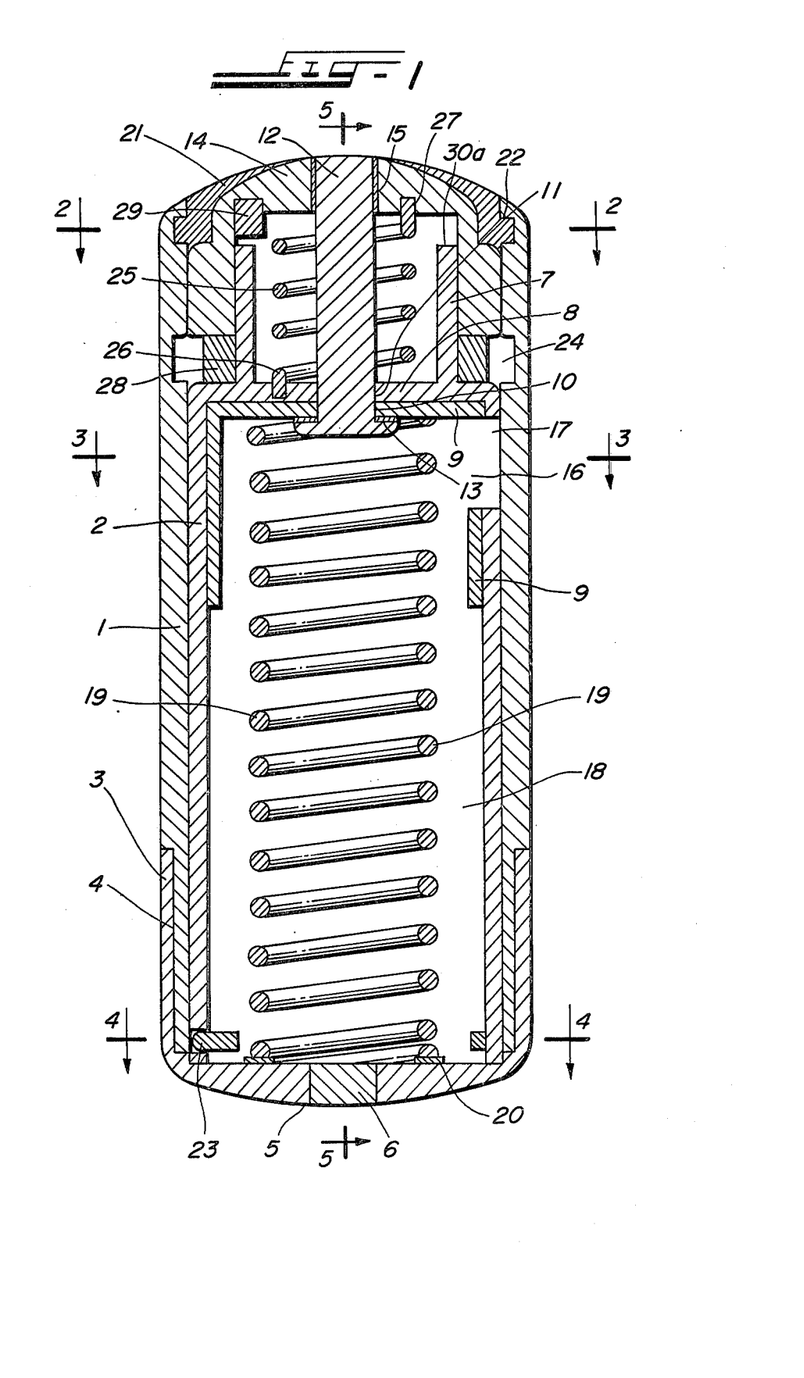
FIG. 1 is in axial section view of one embodiment of the sampling capsule device in initial position.

Considering the construction of the sample device in more detail, with reference to FIG. 1, the outer shell 1 has a bottom or cover 3 which is connected to the main body portion of the shell 1 for example, by way of screw threads (not shown) and with vacuum grease indicated at 4 providing a seal between the bottom member and the main body portion. Bottom 3 is provided to simplify assembly of the working mechanisms of the capsule during manufacture and to facilitate access to the sample of gastric fluid stored in the chamber 18 after use of the device to enable analysis of the sample. Shell members 1 and 2 are so fit together and tightened by help of vacuum grease or O-rings, to create a hermetically sealed capsule. All the parts of the capsule, except the mass are made of materials, such as teflon or an acid resistant steel which are resistant to fluids normally present in the alimentary canal. The bottom 3 has an opening 5 filled with a plug 6 which allows air to be evacuated from chamber 18 as by inserting a needle probe of suitable vacuum pump or syringe through plug 6, providing an under pressure in chamber 18. The plug 6 is of material having characteristics providing self sealing when the needle is withdrawn.

The inner shell 2 has a neck 7 extending perpendicular to a horizontal wall 8, hereinafter referred to as the base of the neck. As shown best in FIG. 9, the height of the neck, which is of hollow cylindrical configuration, is differentiated with the circumference of the upper portion of the neck having a stepped configuration defining stop surfaces 30a and 30b. Under the base of neck 8 is placed the cylindrical valve sleeve 9. The valve sleeve 9 and the neck base 8 have central apertures 10 and 11 of the same inner diameters which makes it possible to thread them onto the shank of a pivot pin 12. The valve sleeve 9 is permanently connected to pin 12 in a suitable manner, such as by a layer of epoxy 13. The inner shell 2, which threaded onto the pin 12, can rotate freely around the axis of pin 12. On neck 7 is placed a header 14 which can rotate around the neck 7. Header 14 is permanently connected to the pin 12 such as by a layer of epoxy 15. In this way, the rotation of the header 14 around neck 7 causes the rotation of sleeve 9 around the inner shell 2. Header 14, pin 12, sleeve 9 and torque 25 form the valve mechanism of the capsule.

The inner shell 2 has rectangular window 17 formed in its side wall and it has the same shape and size as window 16 formed in the side wall of the valve sleeve 9. The windows 16 and 17 are disposed so that in the initial condition (FIGS. 1 and 5) the valve is in flow permiting position and the capsule is in its closed and compressed position, with the openings in alignment with one another. In this position, the chamber 18 is out of communication with the external environment because windows 16 and 17 are covered by the inner wall of outer shell 1. The spring 19 which extends within chamber 18 has its bottom end permanently fastened to bottom member 3, for example by layer of epoxy 20. The top end of the spring engages the under surface of valve sleeve 9. When the capsule is in the closed position, the spring 19 is compressed, exerting a force along the longitudinal axis of the capsule tending to separate shells 1 and 2.

This movement is prevented by the layer of mass 21 disposed in a space between a groove 22 formed in the outer shell 1 and head 14. The mass 21 secures header 14 to the shell 1 and in this way effectively neutralizes the action of the spring 19, and prevents the capsule from expanding.

When in use the capsule G comes into contact with the gastric fluid, mass 21 reacts and loses the properties that enables it to hold the two shells together and thus retard the action of the spring 19. This permits the spring 19 to move the inner shell and the outer shell 1 apart and the capsule assumes its open configuration to the configuration shown in FIG. 6. Complete separation of the two shells 1 and 2 of the capsule is prevented by an expansion spring 23, normally compressed as shown in FIG. 4, and which expands into a groove 24 formed in the inner wall of outer member 1 as the shells 1 and 2 are moving apart as shown in FIG. 6.

When the capsule expands, chamber 18 is enlarged to almost twice its initial capacity and is communicated with the environment through the openings 16 and 17 (FIG. 6) which are uncovered as the result of the separating movement of members 1 and 2. As result of the underpressure in chamber 18, the gastric fluid will aspirate into the inner of chamber 18 through the openings 16 and 17.

Referring to the valve assembly, the torque spring 25 is located in the neck of inner shell 2 with its lower end 26 fastened to the neck base 8 and its upper end 27 fastened to header 14. In the closed position of the capsule, the spring 25 is wound up so it tends to rotate header 14, and together with it, the rest of the valve mechanism around neck 7. But the action of spring 25 is neutralized by the layer of mass 28 placed in a space between neck 7 and header 14. The mass 28 secures the head 14 to the neck 7 and prevents movement of the valve mechanism as long as the mass 28 is intact. After the capsule has expanded (FIG. 6), the space where mass 28 disposed is exposed to the gastric fluid and as result, it loses the properties that permited it to hold head 14 to the neck 7 and thus prevent the movement of the valve mechanism. This allows spring 25 to rotate the assembly including header 14, pin 12 and sleeve 9 through 180°. In this way, the opening 16 in sleeve 9 is moved from the opening 17 in the wall of the inner shell 2 (FIG. 7), causing the capsule to be closed to the environment. The sample of gastric fluid in the chamber 18 is thus sealed in and is secured of contamination as the capsule continues its way through the rest of the digestive tract. The turning of valve sleeve 9 around the inner shell 2 is limited to 180° by a stop member 29 fastened to header 14, and which engages a vertical surface 30a of neck 7 (FIG. 1). At its other extreme of travel, stop member 29 engages surface 30b of the neck 7 as shown in FIG. 2.

After the capsule has passed through the digestive tract, it is recovered from the fecies and washed, and then sent to a laboratory for analysis of the sample. In the laboratory, bottom 3 and spring 19 fastened to 3 are removed as shown in FIG. 8, and the rest of the capsule serves as a tube which encloses the sample for use by the clinical technician during testing.

Figure 2:
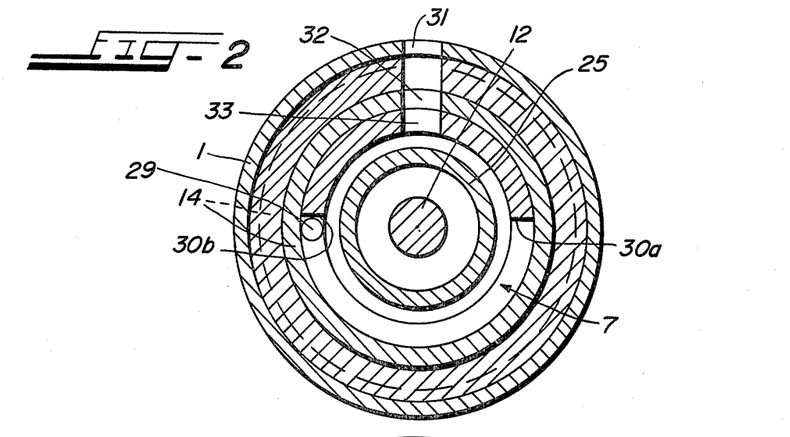
FIG. 2 is a sectional view taken along lines 2—2 of FIG. 1.
Figure 3:
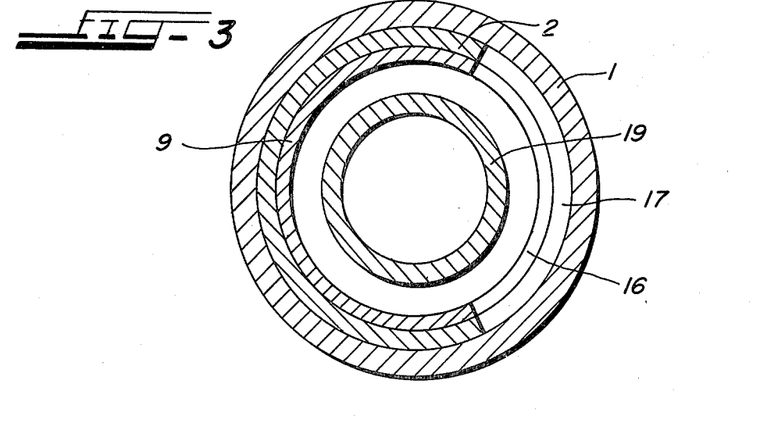
FIG. 3 is a sectional view taken along the lines 3—3 of FIG. 1.

Referring to FIGS. 2 and 5, for the purpose of providing for pre-biasing of springs 19 and 25 during assembly of the device, the outer shell 1 has opening 31, which has the same diameter as an opening 32 formed in header 14 and an opening 33 formed in neck 7. The openings 31, 32, 33 and pin 34 (FIG. 5) simplify set-up of the capsule. During set-up, torque spring 25 is first wound by rotating head 14 180° around neck 7 until the opening 32 and 33 overlap and it is possible to insert peg 34 through the openings. Next the layer of mass 28 is applied, and when it becomes set, the peg 34 is removed. Then the inner shell 2 is slid along the outer shell 1 until the openings 31 and 32 are aligned, and it is possible to pass peg 34 through them. Then the layer of mass 21 is applied and after it becomes set, the peg 34 is removed. The set-up of the capsule is finished by inserting the spring 19 in chamber 18 and the ring spring 23, and securing the bottom 3 on the main body portion of the outer shell 1.

Figure 10:
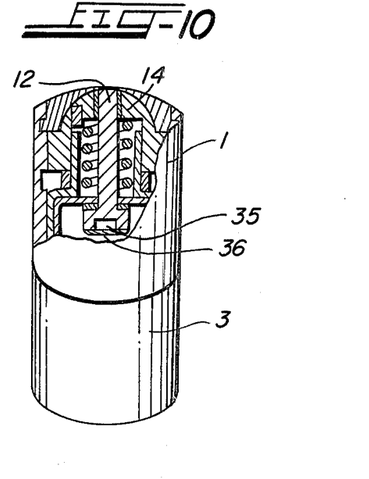
FIG. 10 is a side elevation view, partially in section of a second embodiment of the capsule.

Referring to FIG. 10, the capsule can be used to detect the present of free HCl in the gastric fluid.

Capsule A is constructed identically with capsule G, with the difference that in its inner chamber 18, a container 35, which is secured to or formed integrally with the bottom of pin 12, holds a small quantity of a basic-acid indicator which upon contact with free HCl in the fluid sample received in chamber 18 causes a color change of the fluid sample also. A portion of the walls of the shell members 1 and 2 of capsule A is made of transparent material so that the color change is visible through the transparent wall of the capsule. On the basis of the color of the sample. a determination can be made as to the normal or unnormal composition of the patient's gastric fluid. On example of indicator of free HCl which can be used is dimetylaminoazobenzol which may be in powdered form. The powder is covered with a film of gelatin to delay exposure of the indicator to the fluid until after the valve operates to close the chamber.

Alternatively the capsule may be used to determine the presence of lactic acid in the gastric juice. Tis capsule referred as capsule LA (lactic acid) is constructed exactly as capsule A, with the difference that the indicator, when contacting lactic acid in the sample of gastric fluid, causes coloring of the sample characteristic of the presence of lactic acid. Such indicator is covered this same film as capsule A. Again, the color of the sample may be viewed through the transparent wall of the capsule to determine the existence or non-existence of lactic acid in the gastric fluid of the patient. One example of an indicator of lactic acid which can be used is $FeCl_3$. As an indicator, a paper or other sorbent which contains or is saturated with suitable chemicals may be used.

Figure 11:
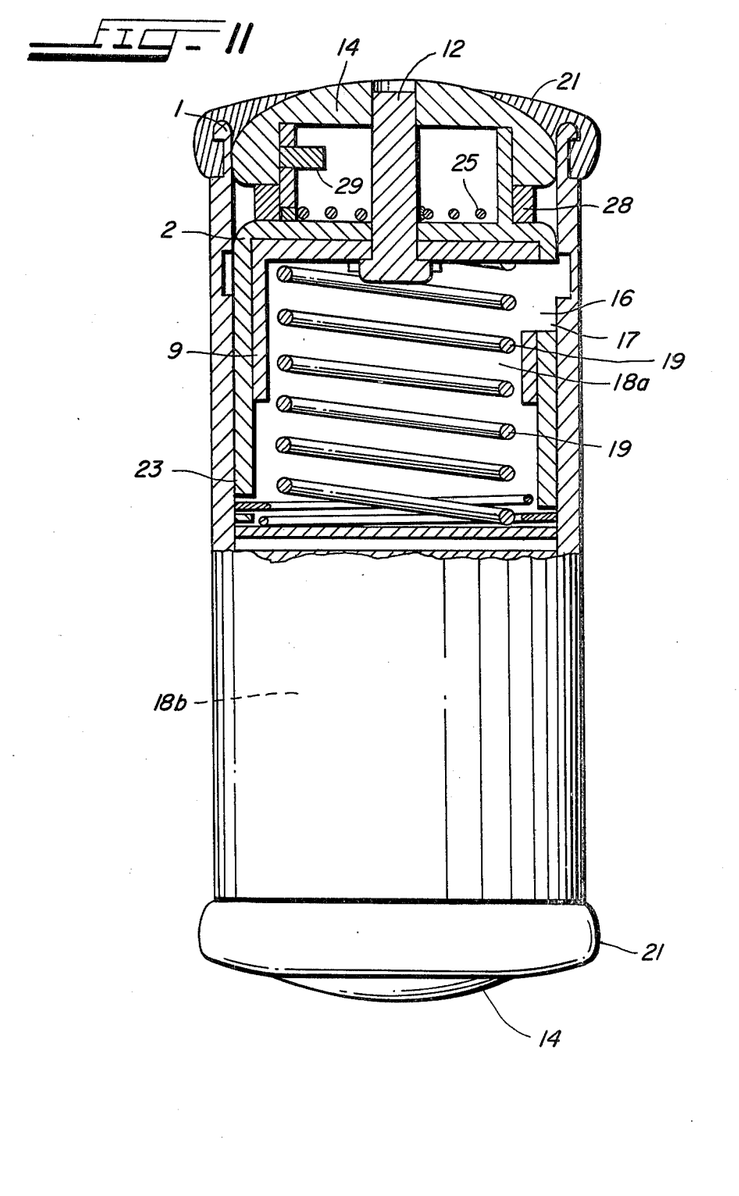
FIG. 11 is a breakaway view of a third embodiment of the capsule.

In FIG. 11 there is shown a further embodiment of the capsule having two separate fluid storage chambers 18a and 18b each having an associated valve mechanism similar to that used in capsule G, for example. Each section of the capsule is similar to that described with reference to the embodiment of FIG. 1 with the mass 21 and 28 that neutralizes the spring 19, embodied as a flat power spring, and valve member 9, respectively, for one of the chambers 18a, being the type responds to gastric fluid, and the mass associated with the other chamber 18b being the type that responds to intestinal fluids. The stop member 29 wich limits rotation of valve sleeve 9 extends from the side wall of the header 14. Thus, this capsule may be used to obtain samples of both gastric fluid and intestinal fluid, or may use the same mass but different indicators forming a combination capsule A and LA. The operation and construction of the sampling device is apparent from foregoing description. It is apparent that one or both of the chambers may be provided with an indicator, as in capsule A or LA, the mass for each section of the device being selected in accordance with its intended use.

Figures 12, 13, 14:
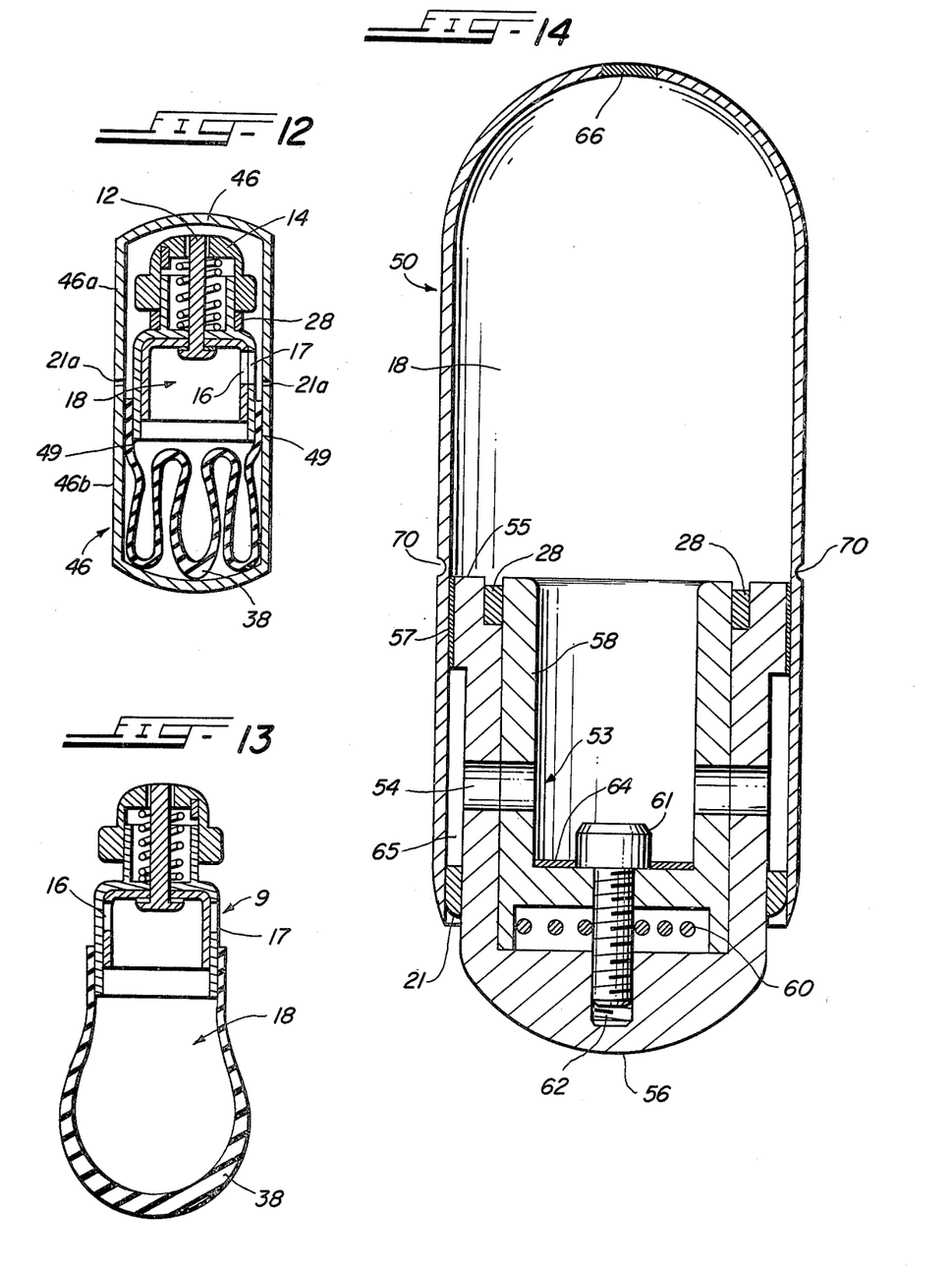
FIGS. 12 and 13 are sectional views of a fourth embodiment of the capsule illustrating unoperated and operated configurations, respectively.
FIG. 14 is a sectional view of a fifth embodiment of the capsule.

Referring to FIGS. 12 and 13, there is shown a modification of the capsule in which capsule chamber 18 is defined in part by a container 38 of an elastic material, which is normally folded up and contained, along with a valve mechanism within a capsule shaped container 46 of a material that is insoluable in fluids of the alimentary canal. The valve mechanism is similar to that employed in the capsule G shown and described above with reference to FIG. 1. The container 38 is hermetically sealed to the base of the inner shell member at points 49. The opening to the chamber 18, is defined by window 16 in valve sleeve 9 and window 17 in the side wall of the inner shell member 2A. The envelope 46, which can be made of material insoluable in alimentary canal's fluids, consists of at least two parts 46a and 46b which are glued together by means of mass 21 which after contact with a suitable fluid of alimentary canal loses the properties that glued the parts 46a and 46b together. Consequently, the envelope breaks apart, allowing the elastic container 38 to expand as shown in FIG. 13. Referring again to FIG. 12, the valve is normally maintained in fluid permitting condition so that when the capsule breaks away, and the container expands, fluid is aspirated into chamber 18 due to the vacuum created as the container 38 expands. After the fluid in the alimentary canal contacts the mass 28 which neutralizes the valve operation, it changes its properties, allowing the valve to close the entrance to the container to seal the fluid within by rotating sleeve 9 to move window 16 out of alignment with window 17. The cover 46 can also be made of material that is soluable in suitable fluids of the alimentary canal. It is pointed out that the container 38 may be of other configurations such as a bellows-shaped, normally compressed and expandable coaxially of the capsule.

Referring to FIG. 14, there is shown a further embodiment in which the mass 21 is employed to seal the entrance way 65 to the openings 53 and 54 of the inner chamber 18. When the mass 21 changes its properties, fluid is permitted to flow into the chamber through openings 53 and 54 and when received within the chamber 18 will cause mass 28 and 64 to changes its properties and allow the valve mechanism to rotate and close the openind 54.

More specifically, a hollow shell member 50 is permanently connected to a flange 55 at the base of a header 65 by a layer of epoxy 57, applied circumferentially, which also seals the shell and the header at the connection. The inner chamber 18 is communicated with the external environment through openings 53 and 54 formed in the side walls of the valve sleeve 58 and the header 56, respectively, and a channel 65 provided by spacing between the capsule 50 and the valve sleeve 56. Channel 65 is normally blocked by mass 21.

The valve sleeve 58 is secured to the header 56 by mass 28, with openings 53 and 54 being in register, and the action of valve spring 60, which is wound up, being neutralized. The spring 60 tends to rotate the sleeve 58 around a pivot pin 61, the shank of which is fixedly received in an aperture 62 formed in the underside of the header 56. A further mass 64 secures the valve sleeve to the pin 61, which is permanently connected to the head 56 by means of a layer of epoxy 62. One end of spring 60 is secured to the pin 61 and other end is secured to the valve sleeve 58 so that when the spring is torqued, the spring tends to rotate the sleeve to move opening 53 out of register with opening 54. As indicated, the spring action is effectively neutralized by the mass 28 and the mass 64. A suitable stop means, not shown, limits rotational movement of the valve member in the manner of stop means 29 shown in FIG. 1.

This device does not use the expansion principle employed in the device of FIG. 1 and may be evacuated to establish an under pressure in the chamber 18 prior to use employing a syringe the needle of which is insertable through suitable self sealing plug 66.

Notches 70 in the side of the container 50 provide break away points for removing the valve assembly and the rest of the capsule serves as a tube which contains the sample for use by the clinical technician during testing.

In use, after the capsule is swallowed by the patient and comes into contact with certain fluids in the alimentary tract, such as gastric fluids, mass 21 changes its properties which otherwise permit it to block the entrance channel 65 to the chamber 18, and a sample of the fluid is aspirated into the chamber 18. When the fluid contacts mass 28 and mass 64, they lose their properties which permitted them to neutralize the operation of the valve. The valve sleeve then rotates under the force of spring 60 to move opening 53 out of register with opening 54 to seal off the chamber 18 with the fluid sample retained therewith.

Figures 15, 16, 17, 18, 19, 20, 21:
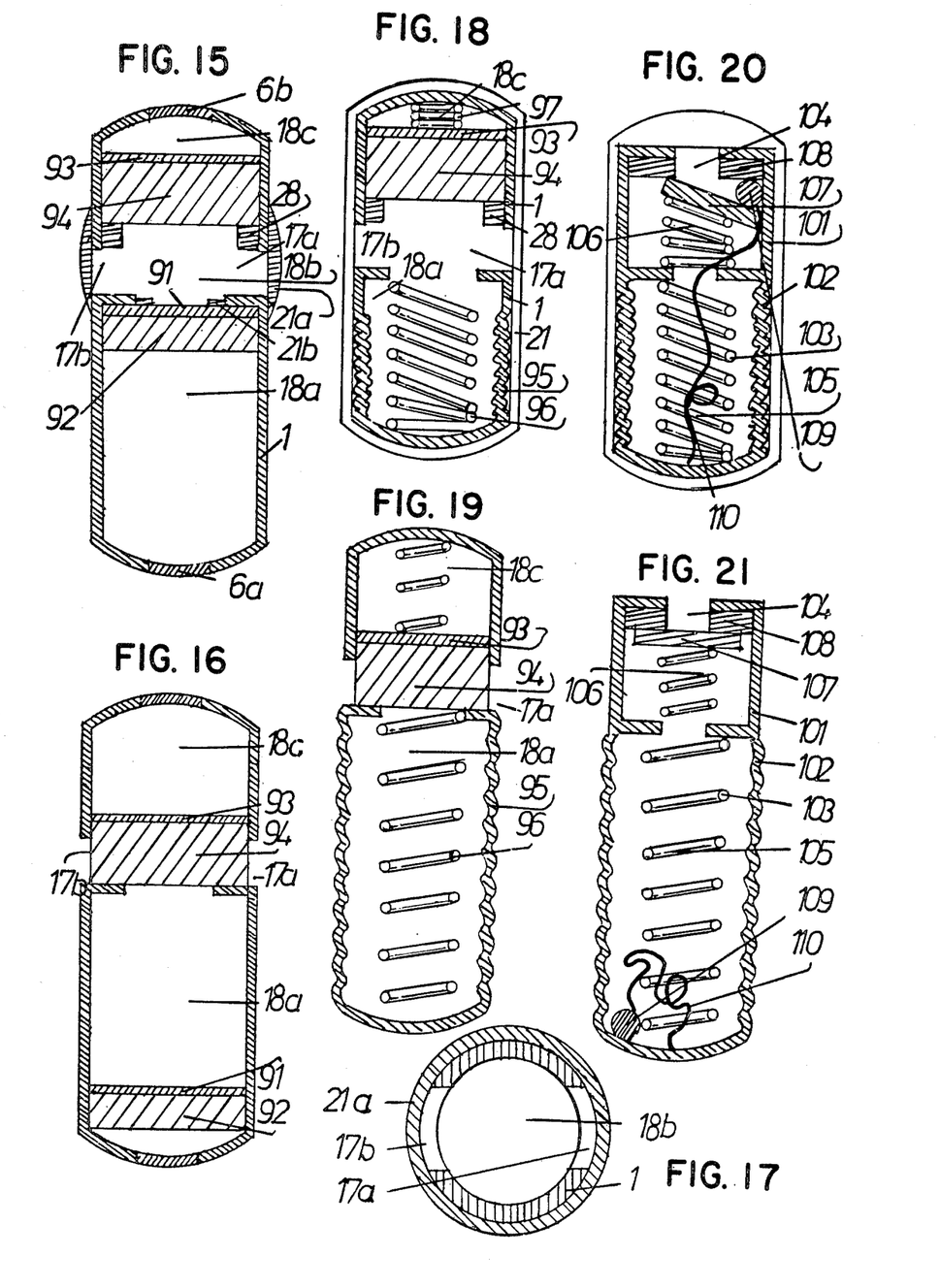

In FIGS. 15-17 there is shown a further embodiment of the capsule. The capsule has the inner chamber 18 which is communicable with the external environment through openings 17a and 17b formed in the side wall of the capsule. In the chamber there are two discs 91 and 93 made of such material as metal or plastic. The disc 91 is permanently connected to the seal 92 and the disc 93 is permanently connected to the seal 94. The discs 91 and 93 divide the chamber 18 into three portions, 18a, 18b and 18c.

In the chamber 18a an underpressure is established through self-sealing plug 6a as described above with reference to the embodiment shown in FIG. 1, and, similarly, in the chamber 18c an overpressure is established through the plug 6b. In this manner, the seal 92 tends to move downwardly towards the bottom of chamber portion 18a and the seal 94 tends move downwardly to close the openings 17a and 17b. The suction effect of the underpressure is blocked by a mass 21b which glues together the wall 1 of the capsule and the disc 91 in such a way that the seal 92 cannot move. The effect of the overpressure on seal 94 is blocked by a mass 28 which blocks the movement of the seal 94.

The openings 17a and 17b are covered by a mass 21a. In use, after the capsule is swallowed by the patient and comes into contact with suitable fluids in the alimentary tract, mass 21a changes its properties which otherwise permit it to block the openings 17a and 17b, and sample of the fluid is permitted to flow, or be aspirated, into the chamber 18b and when received within the chamber 18b will cause masses 21b and 28 to change their properties which blocked the movement of the the seals 92 and 94. The layer of the mass 28 is much more thick than the layer of the mass 21b so that the holding property of mass 21b is removed first. This permits the underpressure to move the seal 92 and to collect the sample of the fluid, and then, when mass 28 loses its effectiveness, the overpressure in the chamber 18c is able to move the seal 94 and close the capsule, hermetically sealing it as shown in FIG. 16.

In FIGS. 18 and 19 is shown a modification of the capsule in wich the capsule chamber 18 is defined in part by bellows-shaped container 95. The closing means is similar to that employed in the capsule shown and described above with reference to FIGS. 15-17, but the overpressure is replaced by the compressed spring 97, and the underpressure is replaced by the spring means 96 and the bellows-shaped container. The envelope 46 is similar to that employed in the capsule shown and described above with reference to FIG. 12.

As described hereinbefore, the envelope 46, which can be made of material insoluable in alimentary canal's fluids, consists of at least two parts 46a and 46b which are glued together by means of mass 21 which after contact with a suitable fluid of alimentary canal loses the properties that glued the parts 46a and 46b together.

After contact with suitable body fluid, the envelope 46 breaks apart, allowing the bellows-shaped container 95 to expand as shown in FIG. 19. The sample of fluid is aspirated into the chamber 18a due to the underpressure created as the container expands. After the fluid contacts the mass 28 which blocks operation of the spring 97, it changes its properties, allowing the seal 94 to close the openings 17a and 17b as shown in FIG. 19.

In FIGS. 20 and 21 is shown a modification of the device similar to the device shown in FIGS. 18 and 19. The compressed spring 106 tends to close the opening 104 through which the inner chamber is communicable with the exterior of the device. The round block 109 situated between the seal 107 and the O-ring 108 blocks the action of the compressed spring 106 and keeps the opening 104 in the open position. The block 109 is permanently connected with the bottom of the bellows-shaped container 102 by means of the thread 110. The length of the thread 110 is shorter than the length of the expanded device.

After contact with suitable body fluid, the envelope 46, which covers the opening 104 and keeps the spring 105 in the compressed state and keeps the container 102 in its compressed position, breaks apart and provokes the expansion of the container 102, suction of the body fluid, removal of the block 109 from its position between the O-ring 108 and the spring 106, allowing the spring 106 to move the seal 107 to close the opening 104, as shown in FIG. 21.

Having thus disclosed in detail preferred embodiments of my invention, persons skilled in the art will be able to modify certain of the structures which have been disclosed and to substitute equivalent elements for those which have been illustrated; and it is, therefore, intended that all such modifications and substitutions be covered as they are embraced within the spirit and scope of the appended claims.

I claim:

1. A swallowable device for use in the examination of the alimentary canal, said device comprising: a container having at least one inner, sample-receiving chamber and at least one opening defining an inlet port for said chamber; blocking means disposed on and cooperating with said container for maintaining said opening out of communication with the exterior of said container; said blocking means being comprised of a substance of a material having properties which enable it to redissolve following contact with predetermined contents of the alimentary canal, to cause said opening to be communicated with the exterior of the container, allowing a sample to pass from the alimentary canal into said inner chamber; closing means including a sealing member movable to seal off said opening after a sample has passed ino said inner chamber, and operating means for permitting said sealing member to move to seal off said opening only after a sample has passed into said inner chamber.

2. A device according to claim 1 wherein said container comprises a first generally cylindrical member, a second member assembled on said first member and cooperating therewith to define an enclosed container; said first member having an aperture formed through a wall thereof defining said inlet port for said inner chamber of said container and said blocking means maintaining said inlet port out of communication with the exterior.

3. A device as defined in claim 2 wherein said closing means comprises valve means to control fluid flow through said inlet port, and said operating means including a second substance maintaining said valve means in a flow permitting position in which said chamber is communicated with said inlet port, but permitting said valve means to close said inlet port to prevent fluid flow into said chamber through said inlet port after a sample has passed into said chamber, said second substance being of a material that is soluble in said predetermined fluid to permit said valve means to operate to flow preventing position to thereby retain the sample of fluid within said chamber.

4. A device as defined in claim 3 characterized by the fact, that said first substance covers said inlet port to prevent fluid flow through an opening of valve means to the chamber which is maintained at an under pressure, said first substance dissolving in predetermined fluid to thereby communicate said chamber with the exterior through said inlet port and said opening of said valve means.

5. A device as defined in claim 3 characterized by the fact, that said second member comprises an open ended container of an elastic material having its open end disposed around and hermetically sealed to a generally cylindrical wall of said first member at its open end, and said blocking means comprising at least a two piece envelope enclosing said container and said valve means, said envelope pieces being joined together by said first-mentioned substance to thereby permit said envelope pieces to separate upon said predetermined fluid contacting said first substance and altering its properties causing said container to expand, aspirating a sample of the predetermined fluid into the chamber and exposing the second substance to the predetermined fluid to permit said valve means to operate and close the inlet port of the chamber.

6. A device as defined in claim 3 wherein said first and second members are assembled together in telescoping engagement with at least a portion of the wall of said second member covering said inlet port; bias means extending within said chamber for driving said first and second members apart, said first mentioned substance neutralizing the action of the bias means to maintain said first and second members in telescoping engagement with the inlet port out of communication with the exterior of the container until the container reaches the place from which the collection of the sample is to made, and said first substance dissolving responsive to contact with said predetermined contents permitting said bias means to drive said first and second members apart, communicating said inlet port with the exterior.

7. A device as defined in claim 3 characterized by the fact that said sealing member comprises a valve element, said operating means including means mounting said valve element on said first member for movement between a first position in which said valve element opens said inlet port and a second position in which said valve element closes said inlet port, and bias means biasing said element towards said second position said second substance neutralizing the action of said bias means whereby said valve element is retained at said first position prior contact with said predetermined contents of the alimentary canal, said second substance dissolving, after contact with said predetermined contents of the alimentary canal, permitting said bias means to move said valve element to said second position thereby closing said inlet port.

8. A device according to claim 1 which comprises an underpressure operated seal disposed to block said opening, a further material which maintains said seal in a position to block said opening, said further material dissolving following contact with predetermined body fluids to permit said seal to operate and unblock the opening into said chamber.

9. A device according to claim 8 wherein said operating means comprises an overpressure for operating said sealing member, and a third substance which prevents the movement of said sealing member until a sample has passed into said chamber, said third substance being of a material which dissolves following contact with a predetermined body fluid to thereby permit said overpressure to move said sealing member.

10. A device according to claim 1 wherein said operating means comprises a spring and a second substance which neutralizes the action of the spring said second substance being of a material which dissolves following contact with a predetermined body fluid to thereby permit said sealing member to move under the force of the spring to seal off said opening.

11. A device according to claim 1 wherein said container comprises a resilient, expandable member said blocking means comprising encapsulating means which encloses said container and maintains said resilient member in a compressed position, at least part of the encapsulating means being of a material which dissolves after contact with predetermined contents of the alimentary canal and provokes the expansion of the resilient member and a corresponding aspiration of the body fluid into the chamber.

12. A device according to claim 11 characterized by the fact, that the closing means comprises a spring which urges said sealing member towards said opening to close the opening through which the inner chamber is communicable with the exterior; said operating means including a member which neutralizes the action of said spring, and means connecting said member to an inner surface of the resilient expandable member in such a manner that with the expansion of said resilient member, the spring urges the sealing member to close the opening.

13. A swallowable device for use in the examination of the alimentary canal, said device comprising: a shell member, enclosing means assembled on said shell member and cooperating therewith to define an enclosed chamber, and for covering an opening in said shell member through which said chamber is communicable with the exterior of the shell member; valve means enclosed within said chamber for controlling fluid flow through said opening, first retaining means including a substance maintaining said valve means in a flow permitting position in which said chamber is communicated with said opening and said valve means being operable under the control of said first retaining means to prevent fluid flow into said chamber through said opening; said enclosing means including second retaining means including a second substance of a material which dissolves following contact with a predetermined fluid present in the alimentary canal, and upon dissolving causes said opening to be communicated with the exterior of the shell member, permitting a sample of the fluid to pass into said chamber, said substance of said first retaining means being of a material which dissolves in said predetermined fluid and upon dissolving permits said valve means to be operated to flow preventing position to thereby retain the sample of fluid within said chamber.

14. A device adapted to be introduced into the alimentary canal comprising: a container having at least one chamber and at least one inlet providing a communication between the interior of the chamber and the exterior, a collecting means able to collect a sample from the exterior into the chamber, a closing means operable to close the inlet, means for operating said closing means, and a blocking means for blocking the collecting means and preventing the contents of the alimentary canal from entering the chamber during the travel of the container through the alimentary canal prior to the container reaching the place from which the collection of the sample is to be made, and for preventing the operation of the closing means prior to the collection of the sample; said blocking means comprising a material responsive to the contents of the stomach, in that the blocking means loses its blocking property whereby the chamber is communicated with the exterior and a sample of the contents of the alimentary canal is able to enter the chamber, and the collecting means and the closing means are actuated, and said material being disposed in such a way that the collecting means is actuated prior operation of the closing means, allowing the collection means and the closing means to act, respectively in the stomach, and to collect the sample into the chamber automatically, without an external intervention and free of contaminations derived from the oral cavity and the esophagus and from the sections following the stomach.

15. A device as defined in claim 14, wherein the blocking means consists of a material from the group consisting of gelatin, carbohydrates, gum arabic, proteins, celluloseacetate phthalate, shellac, polyacryl, polyvinyl chloride, or mixtures or derivatives thereof.

16. A device according to claim 14, wherein said blocking means comprises a material which is selectively responsive to the contents of the alimentary canal, and which, during the travel of the container through the alimentary canal, loses its blocking property only in response to contact with the contents of predetermined sections of the alimentary canal and other than the stomach, whereby samples can be collected from different and predetermined sections of the alimentary canal, depending upon the property of the material, allowing the collection of the samples from the predetermined sections of the alimentary canal automatically, and without an external intervention, and the samples being free of contaminations derived from sections other than that from which the sample is collected, because said material is resistant to the contents of the sections of the alimentary canal prior to said predetermined sections but is responsive to the contact with the contents of said predetermined sections of the alimentary canal to lose its blocking property and so allow the collecting means and the closing means to act respectively in said predetermined section of the alimentary canal to collect the sample into the chamber.

17. A device according to claim 16, wherein said container has at least two chambers; each chamber having at least one inlet providing a communication between the interior of the chamber and the exterior, an individually associated collecting means able to collect a sample from the exterior into the associated chamber, and an individually operable closing means operable to close the inlet after the sample is collected; said collecting means being singly blocked by blocking means which differ in their response to the contents of the predetermined sections of the alimentary canal, so that they lose the blocking properties in different sections of the alimentary canal, allowing collection of at least two samples into two separate chambers, from the different and predetermined sections of the alimentary canal.

18. A device according to claim 17, wherein the closing means comprises two rotatable valve members operated by a biasing means.

19. A device according to claim 16, wherein the collecting means comprises an underpressure created in the chamber prior to or during operation of the collecting means.

20. A device according to claim 16, wherein the closing means comprises a piston means operated by an underpressure.

21. A device according to claim 16, wherein the closing means comprises a valve means operated by a biasing means.

22. A device according to claim 16, wherein the closing means comprises a seal means operated by an overpressure.

23. A device according to claim 16 wherein at least part of the blocking means, is in the form of a coating keeping the container in closed and compressed condition until after response to contact with the contents of a predetermined section of the alimentary canal.

24. A device according to claim 16, wherein at least a portion of the wall of the container is made of transparent material.

25. A device according to claim 24, comprising an indicator means which reacts upon contact with the collected sample to change the color of one of said sample and said indicator means.

26. A device according to claim 25, wherein said indicator means is of a material from the group consisting of a basic-acid indicator, $FeCl_3$ or dimethylaminoazobenzol.

27. A device according to claim 26, comprising a means delaying the contact of the said indicator means with the sample in the chamber.

28. A device according to claim 16, wherein at least part of said blocking means covers the inlet into the chammber for preventing the contents of the alimentary canal from entering the chamber and actuation of the collection means and the closing means during the travel of the container through the alimentary canal prior to the container reaching the place from which the collection of the sample is to occur.

29. A device according to claim 16, wherein at least part of the blocking means comprises an envelope enclosing said container for preventing the contents of the alimentary canal from entering the chamber and actuation of the collection means and the closing means prior to the container reaching the place from which the collection of the sample is to occur; at least part of said envelope being selectively responsive to the contents of another section of the alimentary canal, allowing the collection of the sample and thereafter the closing of the inlet to the chamber, respectively in the predetermined section of the alimentary canal.

30. A device according to claim 16, wherein the container is expandible for enlarging the capacity of the chamber during the travel of the container through the alimentary canal; said container being kept in a compressed condition by at least a portion of the blocking means, and the material being responsive to the predetermined contents of the alimentary canal to lose its blocking property and permit the expansion of the container, and the sample being aspirated into the chamber as the container expands.

31. A device acccording to claim 16, wherein the blocking means consists of a material from the group consisting of gelatin, carbohydrates, gum arabic, proteins, celluloseacetate phtalate, shellac, polyacryl, polyvinyl chloride, or mixtures or derivatives thereof.

32. A device according to claim 14, wherein the collecting means comprises an underpressure created in the chamber prior to or during operation of the closing means.

33. A device according to claim 14, wherein the closing means comprises a piston means operated by an underpressure.

34. A device according to claim 14, wherein the closing means comprises a valve means operated by a biasing means.

35. A device according to claim 14, wherein the closing means comprises a seal means operated by an overpressure.

36. A device according to claim 14, wherein at least part of the blocking means, is in the form of a coating keeping the container in closed and compressed condition until after response to contact with the contents of a predetermined section of the alimentary canal.

37. A device according to claim 14, wherein at least a portion of the wall of the container is made of transparent material.

38. A device according to claim 37, comprising an indicator means which reacts upon contact with the collected sample to change the color of one of said sample and said indicator means.

39. A device according to claim 38, wherein said indicator means is of a material from the group consisting of a basic-acid indicator, $FeCl_3$ or dimethylaminoazobenzol.

40. A device according to claim 39, comprising a means delaying the contact of the said indicator means with the sample in the chamber.

41. A device according to claim 14, wherein at least part of said blocking means covers the inlet into the chamber for preventing the contents of the alimentary canal from entering the chamber and actuation of the collection means and the closing means during the travel of the container through the alimentary canal prior to the container reaching the place from which the collection of the sample occurs.

42. A device according to claim 14, wherein at least part of the blocking means comprises an envelope enclosing said container for preventing the contents of the alimentary canal from entering the chamber and actuation of the collection means and the closing means prior to the container reaching the place from which the collection of the sample is to occur; at least part of said envelope being selectively responsive to the contents of another section of the alimentary canal, allowing the collection of the sample and thereafter the closing of the device, respectively in the predetermined section of the alimentary canal.

43. A device according to claim 14, wherein the container is expandible for enlarging the capacity of the chamber during the travel of the container through the alimentary canal; said container being kept in a compressed condition by at least a portion of the blocking means, and the material being responsive to the predetermined contents of the alimentary canal to lose its blocking property and permit the expansion of the container, and the sample being aspirated into the chamber as the container expands.

44. A device according to claim 14, wherein the blocking means consists of a material from the group consisting of gelatin, carbohydrates, gum arabic, proteins, celluloseacetate phtalate, shellac, polyacryl, polyvinyl chloride, or mixtures or derivatives thereof.

* * * * *